United States Patent
McCready et al.

(10) Patent No.: US 8,712,548 B2
(45) Date of Patent: Apr. 29, 2014

(54) PULL THROUGH CORONARY SINUS PACING LEAD

(75) Inventors: James McCready, Steyning (GB); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

(21) Appl. No.: 13/560,746

(22) Filed: Jul. 27, 2012

(65) Prior Publication Data
US 2013/0030512 A1 Jan. 31, 2013

Related U.S. Application Data

(60) Provisional application No. 61/574,150, filed on Jul. 28, 2011.

(51) Int. Cl.
*A61N 1/00* (2006.01)
(52) U.S. Cl.
USPC .......................................................... 607/119
(58) Field of Classification Search
USPC .................................................. 607/115–122
See application file for complete search history.

(56) References Cited

U.S. PATENT DOCUMENTS 6,185,464 B1 * 2/2001 Bonner et al. ................. 607/119
6,711,443 B2 3/2004 Osypka

OTHER PUBLICATIONS

Worley, Seth J., et al.; Goose Neck Snare for LV Lead Placement in Difficult Venous Anatomy; © 2009, The Authors, Journal compilation © 2009 Wiley Periodicals, Inc. PACE, vol. 32; Dec. 2009; pp. 1577-1581.

* cited by examiner

*Primary Examiner* — Rex R Holmes
(74) *Attorney, Agent, or Firm* — Edwards Wildman Palmer LLP; Scott D. Wofsy; Alicia J. Eposito

(57) ABSTRACT

A coronary sinus lead is disclosed that includes a lead body having opposed proximal and distal end portions, and an open-ended cavity formed in the distal end portion of the lead body for temporarily receiving an angioplasty balloon. The lead is configured for connection with a pacing device. A method of implanting the lead is also disclosed, which includes passing a coronary angioplasty balloon catheter over a length of guide wire extending through the coronary sinus, coronary veins, and collaterals so that the balloon is externalized. The method further includes inserting the balloon into an open cavity of the lead, inflating the balloon within the open cavity to temporarily engage a distal end portion of the lead to the catheter, and pulling the distal end portion of the lead though the coronary sinus and into a coronary vein by at least partially withdrawing the catheter from the coronary sinus.

6 Claims, 7 Drawing Sheets

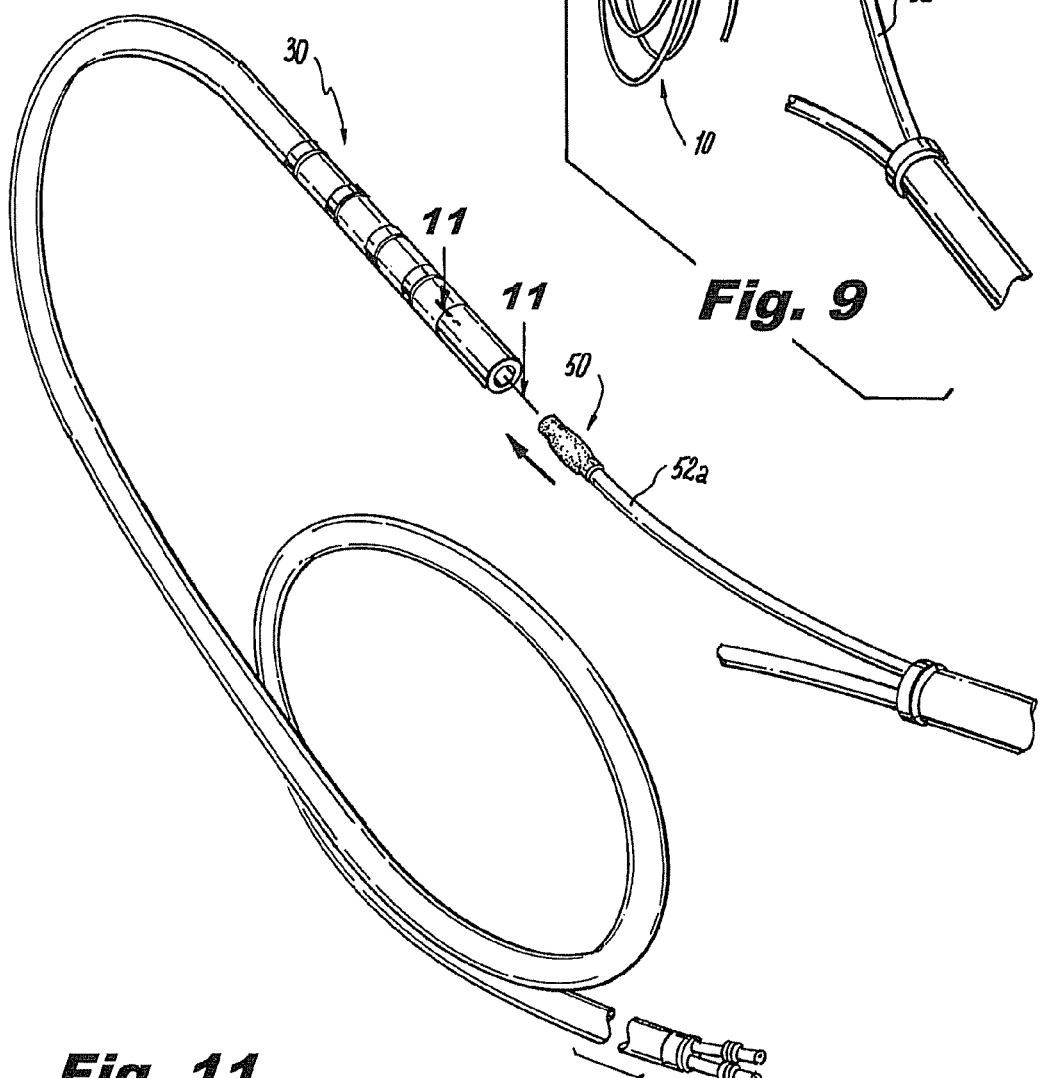

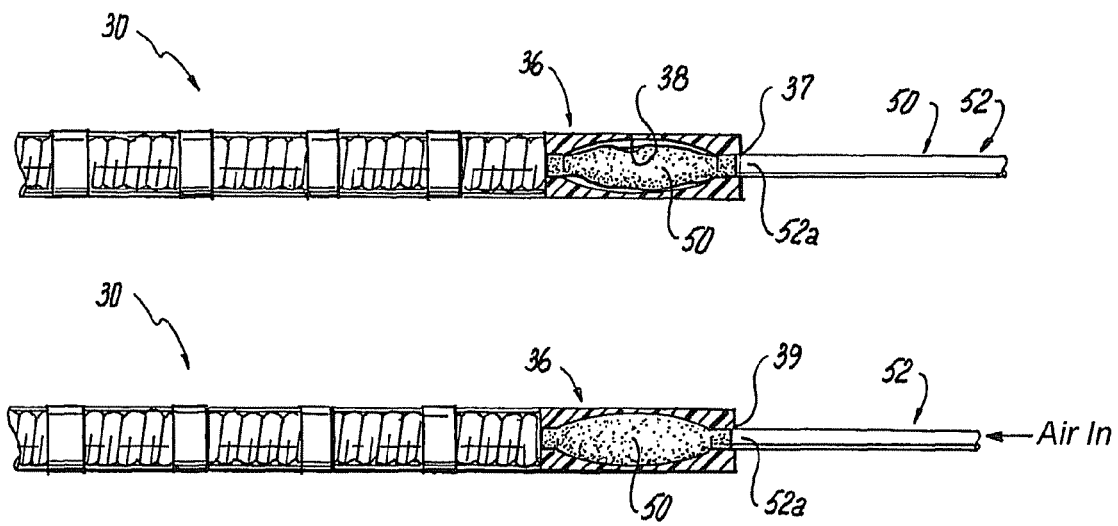
Fig. 12
Fig. 13
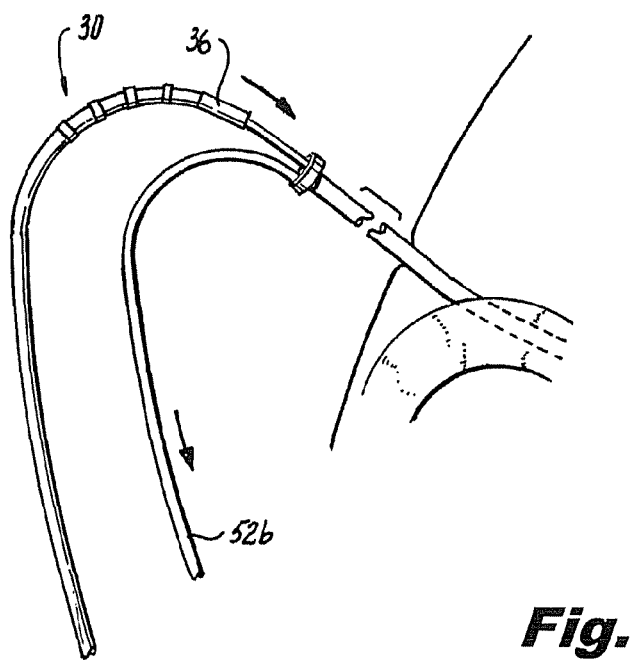
Fig. 14

PULL THROUGH CORONARY SINUS PACING LEAD

CROSS-REFERENCE TO RELATED APPLICATION

The subject application claims the benefit of priority from U.S. Provisional Patent Application Ser. No. 61/574,150 filed Jul. 28, 2011, the disclosure of which is herein incorporated by reference in its entirety.

BACKGROUND OF THE INVENTION

1. Field of the Invention

The subject invention is directed to an implantable coronary sinus lead for left ventricular pacing and to a method of placing or otherwise implanting such a lead in the coronary sinus vein.

2. Background of the Related Art

It has been found that cardiac stimulation can have a beneficial effect in treating congestive heart failure. However, pacing therapy for treating congestive heart failure often requires left ventricular stimulation, either alone or in conjunction with right ventricular stimulation and defibrillation. Left ventricular pacing presently requires placement of an epicardial lead by way of a thoracotomy, which is a high risk procedure performed under general anesthesia.

To obviate the need for a thoracotomy, left ventricular access leads have been developed which are introduced through the coronary sinus and then advanced through the coronary veins so that the distal electrode of the lead can be positioned on the surface of the left ventricle of the heart, as disclosed for example in U.S. Pat. No. 6,711,443 to Osypka, the disclosure of which is herein incorporated by reference in its entirety.

The coronary veins of the heart are of a relatively small diameter. The pacing lead extended therethrough must therefore be of a relatively small diameter compared to pacing leads used for right ventricular stimulation. However, these leads are typically advanced into the coronary veins over guide wires or with the support of a stylet extending through a central lumen formed in the lead body. This central lumen tends to increase the overall diameter of the lead body and limits how small the lead diameter can be constructed. Furthermore, because existing leads are pushed into the coronary veins, sometimes with the support of guiding catheters, the tortuosity and stenosis in the coronary veins can impede the progress of the lead, limiting its ideal placement.

While such devices and techniques have generally been considered satisfactory for their intended purpose, there is a need in the art for smaller pacing leads and improved delivery methods.

SUMMARY OF THE INVENTION

The subject invention is directed to a new and useful coronary sinus pacing lead, and more particularly, to a method of placing or otherwise implanting the pacing lead in the coronary sinus vein of the heart for biventricular pacing or cardiac resynchronization therapy (CRT). The novel method includes the steps of passing a distal end portion of an angioplasty guide wire from the coronary sinus, through coronary veins, across collaterals and back into the coronary sinus, and subsequently snaring the distal end portion of the guide wire located within the coronary sinus using a surgical tool such as a goose neck snare extended into the coronary sinus from the distal end of a guide catheter.

The method further includes the steps of externalizing the distal end portion of the guide wire outside of the patient by withdrawing the snare from the coronary sinus, and thereafter passing a coronary angioplasty balloon catheter over the length of the guide wire so that the balloon is externalized outside the patient.

The method also includes the step of providing a coronary sinus pacing lead having an open cavity formed in a distal end portion thereof for receiving the balloon of the angioplasty catheter. The sinus lead of the subject invention does not have an interior lumen. This allows for a relatively small cross-sectional diameter (e.g., 2-3 French) as compared to the smallest standard coronary sinus leads that are 4 French (F) in diameter. Larger leads may also be utilized for the methodology of the present invention.

The coronary sinus lead of the subject invention can be presented in a bipolar configuration, where one electrode represents the cathode and the other electrode represents the anode. Such a bipolar lead would have a standard bipolar (e.g., IS-1 or IS-4) connector at the proximal end thereof.

Alternatively, the coronary sinus lead of the subject invention could be configured with four electrodes, where the two distal-most electrodes are connected in parallel and represent the cathode, and the two proximal-most electrodes are connected in parallel and represent the anode. In this embodiment, the proximal end portion of the lead would have a bifurcated connector portion with two bipolar (e.g., IS-1 or IS-4) type connectors positioned in parallel. In such a case, the implanting physician could select the electrode pair that is most efficient to stimulate the coronary sinus.

The method further includes the steps of inserting the angioplasty balloon into the open cavity of the coronary sinus lead, and subsequently inflating the balloon within the open cavity to temporarily engage the distal end portion of the lead to the catheter. The distal end portion of the coronary sinus lead is then pulled though the coronary sinus and into a coronary vein by withdrawing the angioplasty catheter from the coronary sinus. Thereafter, the balloon is deflated to disengage the catheter from the lead, and the catheter is removed from the surgical site.

These and other aspects of the apparatus and method of the subject invention will become more readily apparent from the following detailed description of the preferred embodiments taken in conjunction with the drawings.

BRIEF DESCRIPTION OF THE DRAWINGS

So that those having ordinary skill in the art to which the subject invention pertains will more readily understand how to make and use the unique coronary sinus pacing lead of the subject invention, preferred embodiments thereof will be described in detail hereinbelow with reference to the drawings, wherein:

FIG. 9 is an illustration of the guide wire being removed from the balloon catheter;

FIG. 10. is an illustration of an end of the balloon catheter and associated balloon being coupled to the coronary sinus pacing lead;

FIG. 11. is an illustration of a bipolar coronary sinus lead constructed in accordance with a preferred embodiment of the subject invention, which includes a distal cavity for receiving an angioplasty balloon, four axially spaced apart ring electrodes including a pair of distal electrodes connected in parallel and configured as a cathode and a pair of proximal electrodes connected in parallel and configured as an anode, and a bifurcated connector portion that includes two connectors;

FIGS. 12-13 are illustrations of the balloon of the angioplasty catheter being coupled to the distal end portion of the coronary sinus lead of FIG. 11;

FIGS. 14-15 are illustrations of the coronary sinus lead being pulled by the coupled angioplasty catheter from an externalized position, through the coronary sinus, coronary veins, and across collaterals.

DETAILED DESCRIPTION OF THE PREFERRED EMBODIMENTS

Figure 1:
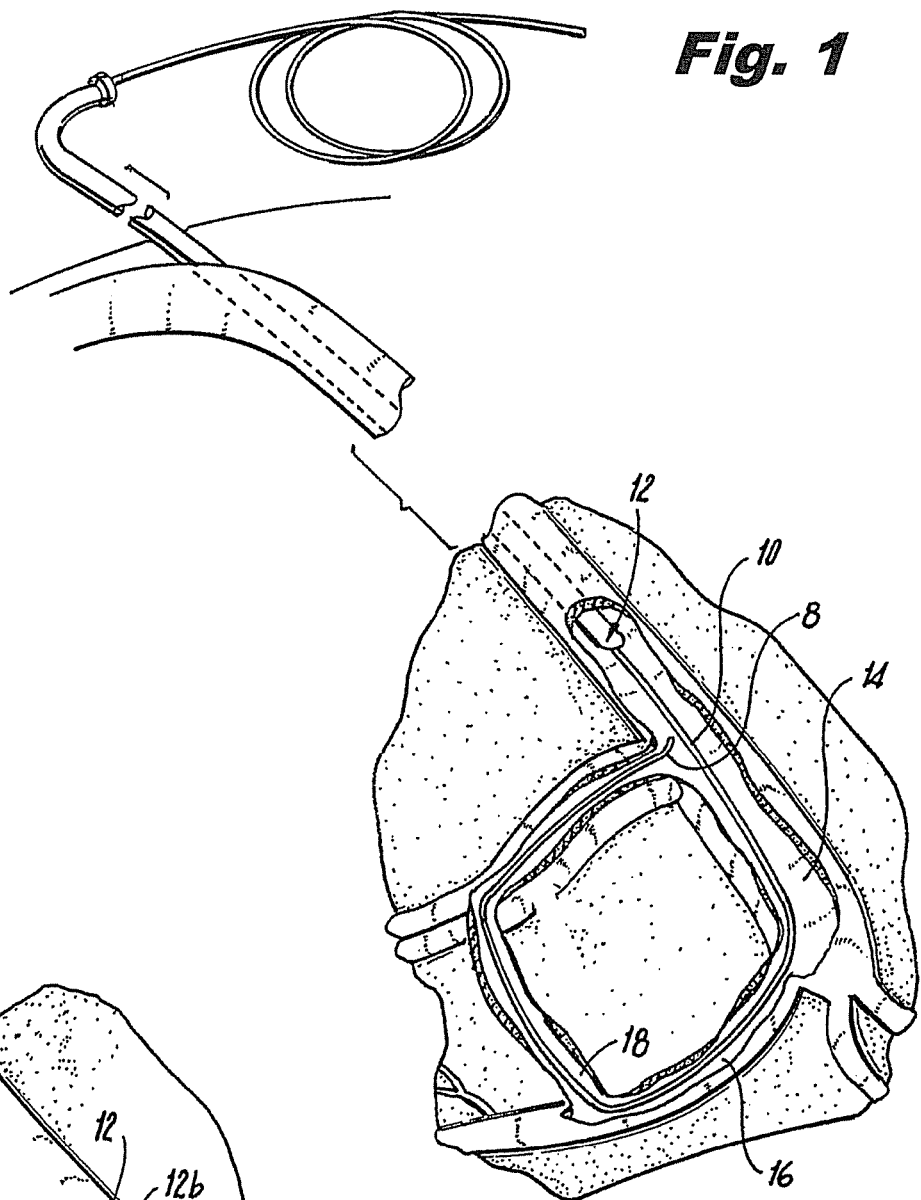
FIG. 1 is a schematic showing the way in which the distal end portion of an angioplasty guide wire, introduced into the vasculature of a patient by a guide catheter, is passed from the coronary sinus, through coronary veins, across collaterals and back into the coronary sinus.

Referring now to the drawings wherein like reference numerals identify similar structural elements or features of the subject invention, there is illustrated in FIG. 1 a representation of the vasculature of a patient, wherein the distal end portion 8 of an angioplasty guide wire 10, has been introduced by a guide catheter 12, and passed from the coronary sinus 14, through coronary veins 16, across collaterals 18 and back into the coronary sinus 14.

Figure 2:
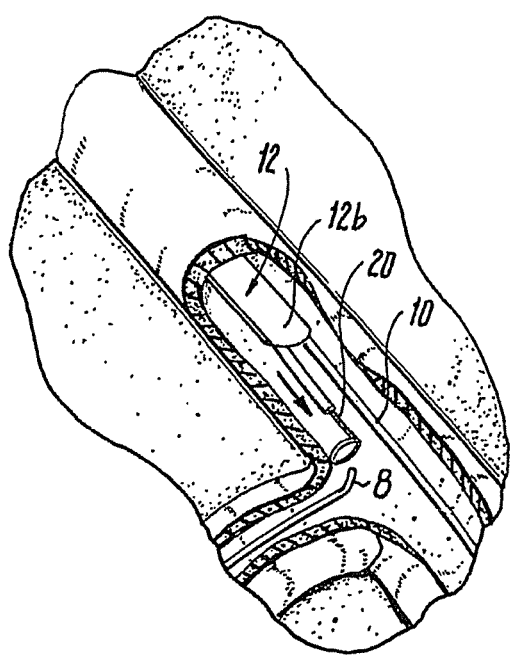
FIGS. 2-5 are schematics showing the way in which a goose neck snare, deployed from the distal end of a guide catheter, is used to capture and externalize the distal end portion of the angioplasty guide wire.
Figure 3:
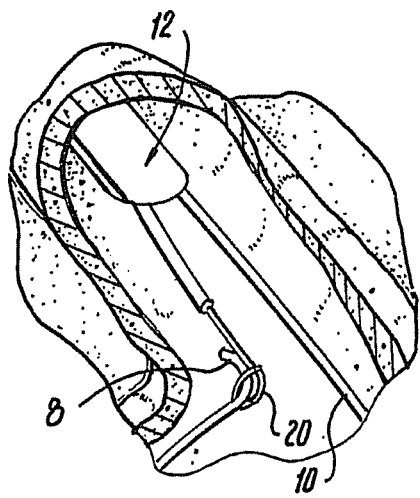
Figure 4:
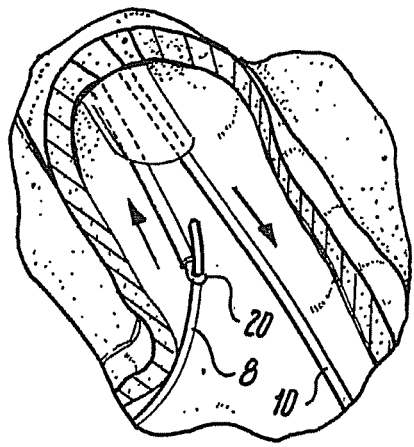
Figure 5:
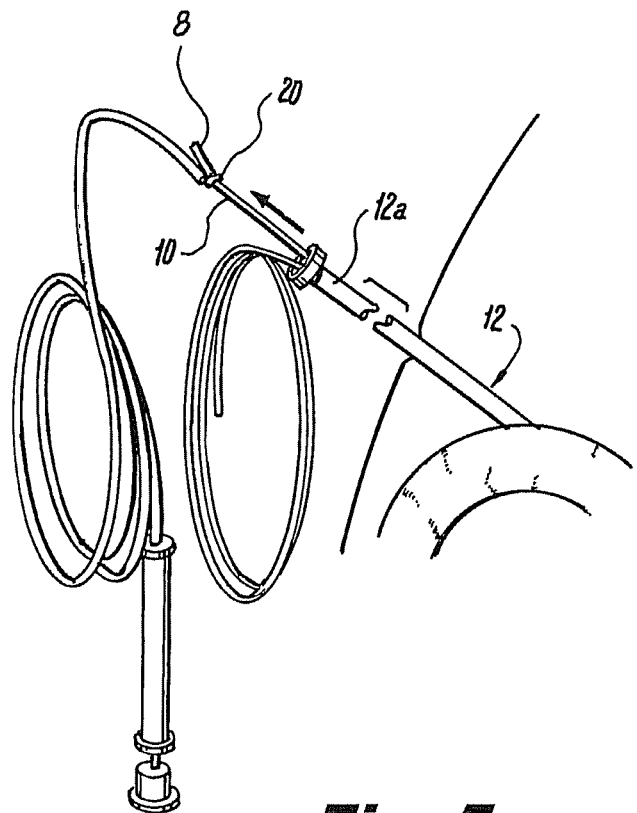

Referring to FIGS. 2-5, a surgical tool such as a goose neck snare 20, deployed from the distal end 12b of the guide catheter 12, is used to capture the distal end portion 8 of the angioplasty guide wire 10 and externalized out of the proximal end 12a of the guide catheter 12 for access by a physician. As best seen in FIG. 2, the goose neck snare 20 is preferably oriented at 90 degrees to maximize a target area for ensnaring the distal end portion 8 of the guide wire 10 as shown in FIG. 3, and for withdrawing (e.g., proximally pulling) the distal end portion 8 as shown in FIG. 4 until the end portion 8 of the guide wire 10 is externalized as shown in FIG. 5. It should be noted that use of a goose neck snare to gain access to the distal end of a guide wire as it re-enters the coronary sinus retrograde via collaterals through an adjacent vein has been described by S. J. Worley et al. (PACE 2009; 32:1577-1581), the disclosure of which is herein incorporated by reference in its entirety.

Figure 6:
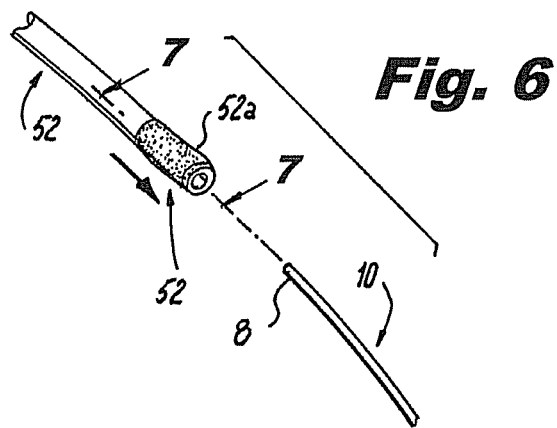
FIG. 6 is an illustration of an end of an angioplasty balloon catheter being passed over the externalized end portion of the guide wire.
Figure 7:
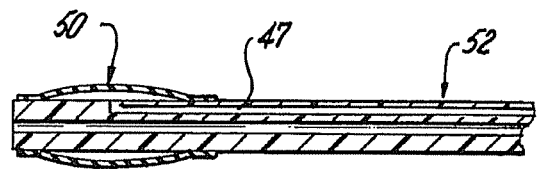
FIG. 7 is a cross-section of an end of the angioplasty balloon catheter and associated balloon in a deflated state.
Figure 8:
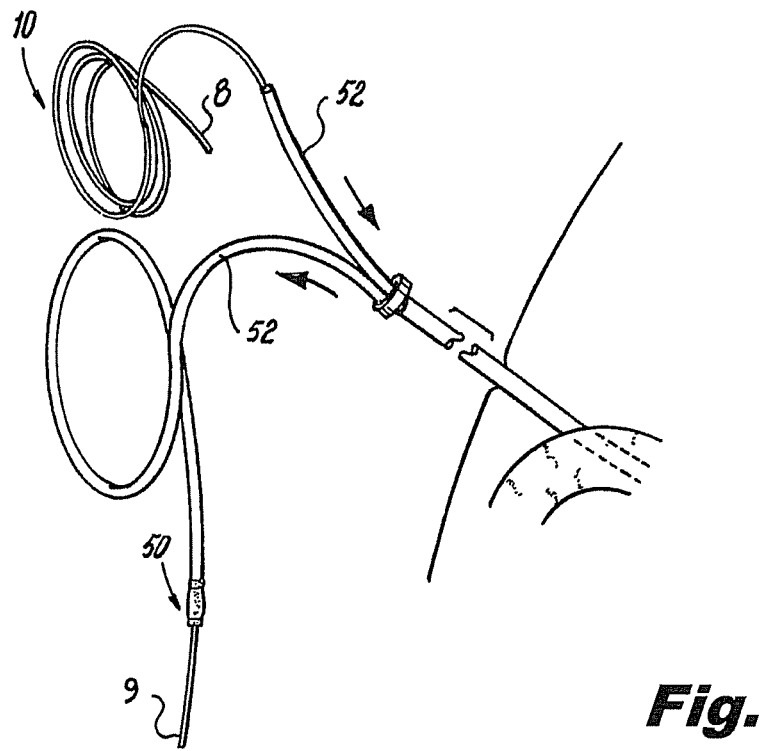
FIG. 8 is an illustration of advancement of the angioplasty balloon catheter over the guide wire until the opposite ends of the balloon catheter are externalized.

Referring now to FIGS. 6-8 with continued reference to FIG. 1, an externalized end 52a of an angioplasty catheter 52 having an angioplasty balloon 50 associated therewith is passed over the externalized end 8 of the guide wire 10 as in FIG. 6, over the length of guide wire 10 extending through the coronary sinus 14, coronary veins 16, and collaterals 18 shown in FIG. 1, back into the coronary sinus 14, and back out over the opposite externalized end 9 of the guide wire 10 as shown in FIG. 8. As shown in FIG. 7, the balloon 50 is fluidly coupled to a lumen 47 of the catheter 52 for supplying air or other suitable fluid thereto for inflating the balloon from a deflated state to an inflated state as further discussed below. As shown in FIG. 9, the guide wire 10 is removed from the angioplasty catheter 52, leaving the catheter 52 traversing the loop originally traversed by the guide wire 10 in FIG. 1.

Referring now to FIG. 10, the externalized end 52a and balloon 50 of the catheter 52 are coupled to a bipolar coronary sinus pacing lead constructed in accordance with a preferred embodiment of the subject invention and designated generally by reference numeral 30. As best shown in FIG. 11, the pacing lead 30 is defined by an elongated lead body 32 having a cross-sectional diameter "d" of about 2-3 F, with opposed proximal and distal end portions 34, 36. Advantageously, pacing lead 30 has no central lumen. A cavity 38 is provided in the distal end portion 36 of pacing lead 30 for receiving the angioplasty balloon 50 of the angioplasty catheter 52. Four axially spaced apart ring electrodes 40a-40d are operatively associated with the distal end portion 36 of lead 30. The distal-most electrodes 40a, 40b are connected in parallel and configured as a cathode, while the proximal-most pair of electrodes 40c, 40d are connected in parallel and configured as an anode. The proximal end portion 34 of lead 30 is bifurcated so as to include connector portions 42 and 44, each having a standard type connector (e.g. IS-1, IS-4) associated therewith. Other types of connectors can also be employed.

As shown in FIGS. 12-13, the angioplasty catheter 52 and the coronary sinus lead 30 are coupled to one another by inserting the angioplasty balloon 50 of the angioplasty catheter 52 in a deflated state through a distally facing opening 37 of the cavity 38 of the lead 30 as shown in FIG. 12, and inflating the balloon 50 within the open cavity 38. Inflating the balloon 50 within the open cavity 38 causes it to temporarily engage the distal end portion 36 of the lead 30 to the catheter 52 by an interference fit as depicted in FIG. 13.

Figure 15:
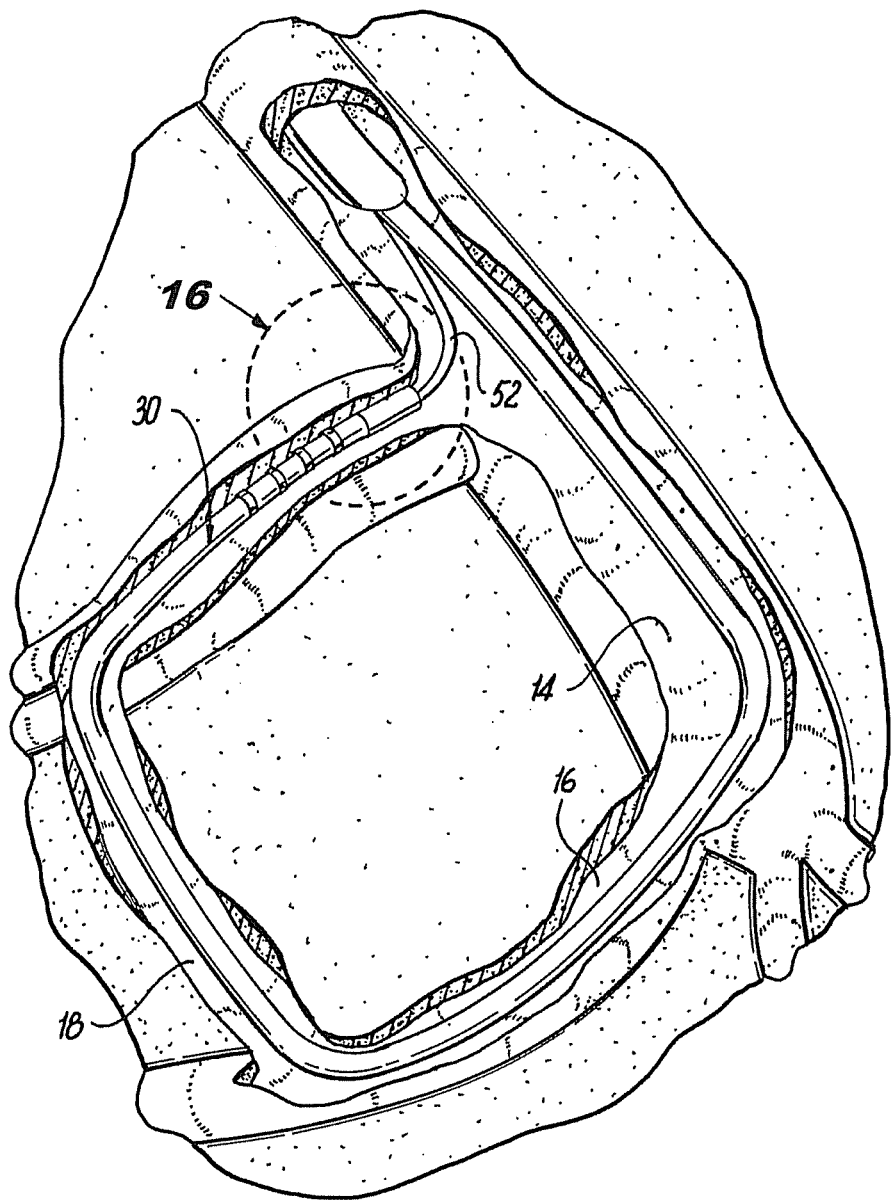

Referring now to FIGS. 14-15, the distal end portion 36 of the coronary sinus lead 30 is then pulled though the coronary sinus 14 and into a coronary vein 16 by at least partially withdrawing the angioplasty catheter 52 from the coronary sinus as illustrated by the arrangement in FIG. 14. For example, partial withdrawal of the angioplasty catheter 52 may be accomplished by pulling the externalized end 52b of the angioplasty catheter 52 opposite the end 52a coupled to the lead 30, causing the catheter 52 to translate through the loop of the coronary sinus 14, coronary veins 16, and collaterals 18, and pulling the coupled lead 30 with it until the lead 30 reaches a desired location, such as, for example, that shown in FIG. 15.

Figure 16:
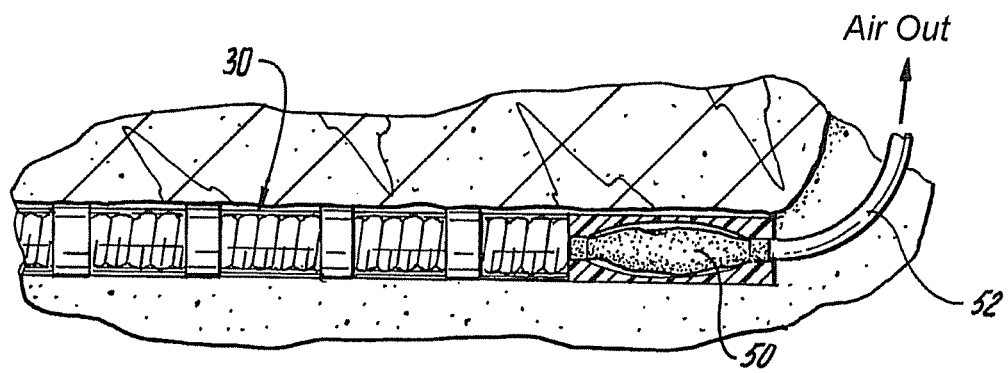
FIGS. 16-17 are illustrations of the angioplasty catheter being disconnected from the coronary sinus lead, leaving the coronary sinus lead in the position of FIG. 15.
Figure 17:
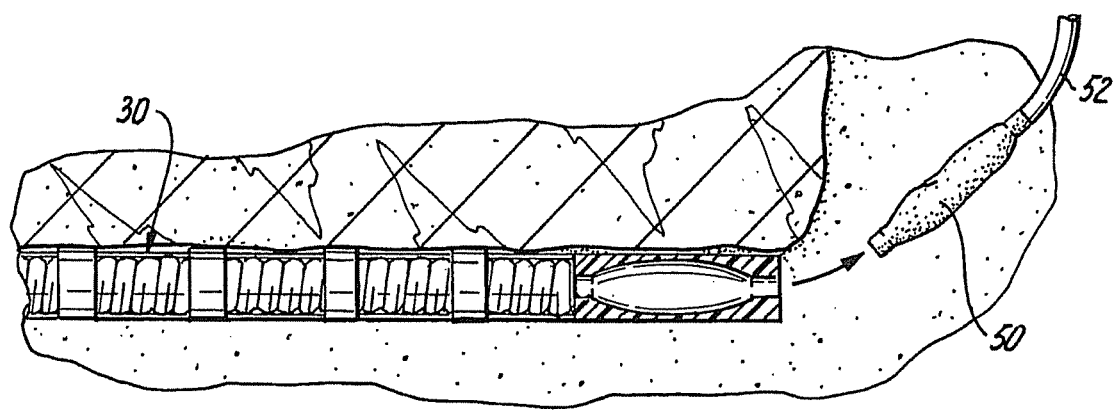

Referring now to FIGS. 16-17, when the lead 30 reaches the desired location, the balloon 50 is deflated as shown in FIG. 16 to disengage the catheter 52 from the lead 30, and the catheter 52 is removed from the surgical site as illustrated in FIG. 17. Thereupon, the implanting physician may select the electrode pair that is most efficient to stimulate the coronary sinus.

While the apparatus and method of the subject invention has been described with respect to preferred and exemplary embodiments, those skilled in the art will readily appreciate that various changes and/or modifications can be made to the invention without departing from the spirit or scope of the invention as described herein.

What is claimed is:

1. A coronary sinus pacing lead, comprising:
   a lead body configured to connect with a pacing device to stimulate cardiac tissue, the lead body having a proximal end portion and an opposed distal end portion, the distal end portion configured to detachably couple to an angioplasty balloon of an angioplasty catheter, wherein the lead body extends between the opposed proximal and distal end portions without a central lumen, the distal end portion defines an open-ended cavity configured to receive an angioplasty balloon, and the lead is configured to connect with a pacing device to stimulate cardiac tissue.

2. A coronary sinus pacing lead according to claim 1, wherein the lead body has a cross-sectional diameter of about 2-3 F.

3. A coronary sinus pacing lead according to claim 1, further comprising:
 a) electrode means operatively associated with the distal end portion of the lead body for stimulating the cardiac tissue; and
 b) connector means operatively associated with the proximal portion of the lead body configured to connect with the pacing device.

4. A coronary sinus pacing lead according to claim 1, wherein the open-ended cavity is defined by a distally facing opening for receiving the balloon.

5. A coronary sinus pacing lead according to claim 1, wherein the open-ended cavity is configured to couple the distal end portion of the lead body to the balloon via an interference fit.

6. A coronary sinus pacing lead according to claim 1, wherein the open-ended cavity is configured to receive the angioplasty balloon in a deflated state, and to couple to the balloon by an interference fit when the balloon is in an inflated state.

* * * * *